United States Patent
Lederer et al.

(10) Patent No.: US 6,458,992 B1
(45) Date of Patent: Oct. 1, 2002

(54) PROCESS AND APPARATUS FOR THE PRODUCTION OF BUTYLACETATE AND ISOBUTYLACETATE

(75) Inventors: Jaromír Lederer, Teplice; Jiří Kolena, Litvínov; Jiří Hanika, Prague, all of (CZ); Willem Wiekert Levering; Oliver Bailer, both of Winterthur (CH); Pavel Morávek, Litvínov-Janov (CZ); Quido Smejkal, Neratovice (CZ); Vladimír Macek, Lithvínov (CZ)

(73) Assignees: Sulzer Chemtech AG, Winterthur (CH); Chemopetrol, A.S., Litvinov (CZ)

( * ) Notice: Subject to any disclaimer, the term of this patent is extended or adjusted under 35 U.S.C. 154(b) by 0 days.

(21) Appl. No.: 09/647,013

(22) PCT Filed: Mar. 11, 1999

(86) PCT No.: PCT/EP99/01583

§ 371 (c)(1),
(2), (4) Date: Dec. 6, 2000

(87) PCT Pub. No.: WO99/48855

PCT Pub. Date: Sep. 30, 1999

(30) Foreign Application Priority Data

Mar. 25, 1998 (CZ) .................................. 901-98
Mar. 25, 1998 (CZ) .................................. 902-98

(51) Int. Cl.$^7$ .................... C07C 69/02; C07C 67/00; C07C 67/48
(52) U.S. Cl. ............... 560/239; 560/231; 560/239; 560/248
(58) Field of Search ............. 560/231, 239, 560/248

(56) References Cited

U.S. PATENT DOCUMENTS 5,430,178 A * 7/1995 Uhm et al.
6,028,215 A * 2/2000 Bessling et al.

FOREIGN PATENT DOCUMENTS

EP 0640583 A2 3/1995

OTHER PUBLICATIONS

Database WPI, Week 9732, Derwent Publications Ltd., London, GB; AN 97–342345 & CN 1 107 136 A (Univ. Guangxi), Aug. 23, 1995, Abstract.

* cited by examiner

*Primary Examiner*—Johann Richter
*Assistant Examiner*—Farhad Forohar
(74) *Attorney, Agent, or Firm*—Townsend and Townsend and Crew LLP

(57) ABSTRACT

The invention relates to a process of butylacetate production by esterification of acetic acid with butanol in the presence of a solid acidic catalyst in which distillatory separation of components runs simultaneously with esterification. Thus, acetic acid and butanol are introduced in defined amounts and in the molar ratio 1:1 to 1:10 into a system, in which the reaction and the distillatory separation proceeds in three zones. The reaction together with distillatory separation of the components with different boiling points run in the reaction zone, while only distillation takes place in lower and upper separation zones. A volatile mixture is separated in the upper separation zone, from which, after being cooled at 5 to 80° C., water and organic phases are separated, the latest being refluxed into the system. The ratio of the feed amount to the organic phase reflux amount is 1:1 to 1:20, the reflux amount representing 60 to 100% of the whole amount of the organic phase. Butylacetate is separated as a high boiling bottoms product. The invention relates also to a process of isobutylacetate production by esterification of acetic acid with isobutyl alcohol in the presence of a solid acidic catalyst in which separation of components by distillation runs simultaneously with esterification.

15 Claims, 2 Drawing Sheets

PROCESS AND APPARATUS FOR THE PRODUCTION OF BUTYLACETATE AND ISOBUTYLACETATE

TECHNICAL FIELD

The invention relates to a process for the synthesis of butylacetate by esterification of acetic acid with butanol by distillation accompanied by chemical reaction utilizing a column in which separation of the reaction products takes place together with the esterification in a catalytically active separation equipment. The invention also relates to a process for the synthesis of isobutylacetate by esterification of acetic acid with isobutyl alcohol by the catalytic distillation method using a column in which separation of the reaction products takes place together with the esterification in a catalytically active separation equipment. The invention also relates to apparatuses for performing said process.

BACKGROUND ART

Butylacetate is prepared by the reaction of butanol with acetic acid by which water is produced besides butylacetate. The reaction is reversible and acidic catalysts are utilized to accelerate it. Mineral acids, especially sulfuric acid, or, more recently, ion exchange resins (EP 066059, DE 3636754), or zeolites and so called solid superacids are utilized for this purpose.

According to the state-of-the-art processes (Petrochemia 1985, 25, 99), almost equilibrium composition is achieved in a reactor, the resulting mixture is then distilled by means of a distillation column to separate a mixture, the composition of which is close to the composition of the butanol-butylacetate-water ternary azeotrope. The amount of the reaction water is not sufficient to distill all butylacetate in the mentioned form, therefore additional water must be added. The volume of the waste water to be subsequently treated is thus increased, which is one of the main disadvantages of the processes known in the art. The said steps are very often combined, i.e. the synthesis takes place directly in the distillation column reboiler. Separation of the organic phase from the water phase of the heterogeneous azeotrope prepares conditions for subsequent separation of butylacetate from butanol by distillation of the organic phase in another distillation column from which a mixture containing butanol, traces of dilute water and a small amount of butylacetate is withdrawn as distillate. This overhead product is recycled while butylacetate of purity usually up to 98% mass. is withdrawn as a bottom product. The separation of unreacted butanol from butylacetate is very difficult because of strong nonideality of the mixture. Not only butanol, butylacetate and water create a ternary azeotrope with minimum boiling point but also butanol with butylacetate as well as butanol with water create binary azeotropes. The water phase separated from the first column distillate is further distilled by use of another distillation column, dissolved butanol and butylacetate being separated as distillate, this mixture being recycled to the process. Complex separation of the esterification reaction mixture components is the main disadvantage of the state-of-the-art processes. There are also serious corrosion problems as an additional disadvantage in those processes which utilize mineral acids as catalysts.

Another variant of the butylacetate synthesis takes a possibility to perform the reaction in a column-reactor packed with the ion-exchange catalyst arranged into two zones (CN 1107136A). There is a partial condenser placed into the column head. The vapours are partly condensed in the condenser, the distillate being refluxed to the upper reaction zone without being split into water and organic phases. This has bad impact on the reaction equilibrium, which is a considerable disadvantage of said system. The vapours, non-condensed in the partial condenser, built in the column head, condense in an external condenser, the condensate being refluxed into the column feed after separation of the water from the organic phases, so the problem of accumulation of low boiling impurities in the upper part of the column remains unsolved. The product is withdrawn from the bottom of the reactor. Maximum purity is only 95 to 98 mass % according to said patent (CN 1107136A).

Isobutylacetate is prepared by the reaction of isobutyl alcohol with acetic acid by which water is produced besides isobutylacetate. The reaction is reversible, acidic catalysts are utilized to accelerate it. Mineral acids, especially sulfuric acid or, more recently, solid acidic catalysts are utilized for this purpose as can be seen e.g. from CZ 191357 and CZ 279562. These catalysts can be ion exchange resins, zeolites, so called solid superacids and the like.

According to the state-of-the-art processes relating to isobutylacetate preparation, almost equilibrium composition is achieved in a reactor, the composition being dependent on the starting molar ratio of the reaction components. The resulting mixture is then distilled by means of a distillation column to separate a mixture, the composition of which is close to the composition of the isobutyl alcohol-isobutylacetate-water ternary azeotrope. The amount of reaction water is not sufficient to distill all isobutylacetate in the mentioned form, therefore additional water must be added to the mixture. The volume of the waste water to be subsequently treated is thus increased, which is one of the main disadvantages of the processes known in the art. Said steps are very often combined, i.e. the synthesis takes place directly in the distillation column reboiler. After separating the organic phase from the water phase of the heterogeneous azeotrope it is possible to separate isobutylacetate from isobutyl alcohol by subsequent distillation of the organic phase in another distillation column. The organic phase, separated from the heterogeneous azeotropic mixture contains isobutyl alcohol, isobutylacetate and a certain part of water. Isobutyl alcohol, the rest of water and small part of isobutylacetate are separated from said organic phase by subsequent distillation. The overhead product, obtained this way, is recycled into esterification while pure isobutylacetate is withdrawn as a bottom product. The separation of unreacted isobutyl alcohol from isobutylacetate is very difficult because of strong nonideality of the mixture. Isobutyl alcohol and isobutylacetate create a binary azeotrope, creating also a ternary azeotrope of a minimum boiling point with water. The water phase separated from the distillate of the first column is further distilled by means of another distillation column, dissolved isobutyl alcohol and isobutylacetate being separated overhead, their mixture being recycled to the process. Complex separation of the esterification reaction mixture components is the main disadvantage of these state-of-the-art processes. There are also serious corrosion problems as an additional disadvantage in those processes which utilize mineral acids as catalysts.

DISCLOSURE OF THE INVENTION

Process for the Production of Butylacetate

The process for the production of butylacetate by esterification of acetic acid with butanol in the presence of a solid acidic catalyst consists according to this invention in introducing acetic acid and butanol in a molar ratio 1:1 to 1:10, the overall amount of the feed per volume unit of catalyst being 0.1 to 10 h$^{-1}$, into the system of three zones in which the reaction and distillation take place, the reaction running simultaneously with distillatory separation of the compounds of different boiling points in the reaction zone, while only separation of components by distillation takes place in the upper and lower separation zones, namely of components forming a minimum boiling point ternary azeotrope in the upper separation zone, the volatile mixture of these compounds being split into water and organic phases after being cooled at 5 to 80° C., the organic phase being refluxed to the upper separation zone, the ratio of the feed to the refluxed organic phase being 1:1 to 1:20, the reflux representing 60 to 100% of the whole amount of the separated organic phase and butylacetate being withdrawn as a high boiling bottoms product.

According to this process, acetic acid and butanol can be introduced into the reaction zone or into the upper separation zone. Alternatively, acetic acid and butanol are introduced into the system separately, acetic acid being introduced into the reaction zone or into the upper separation zone, butanol being introduced into the reaction zone or into the lower separation zone according to this process. Finally, 1 to 99% of the whole amount of butanol is introduced as a mixture with acetic acid into the reaction zone or into the upper separation zone of the system while 99 to 1% of butanol is introduced separately into the reaction zone or into the lower separation zone at the same time, according to this process.

In a preferred embodiment, the process is performed at a molar ratio of acetic acid vs. butanol in the range of 1:1 to 1:1.3, the feed flow per the catalyst volume unit being 0.5 to 5 h$^{-1}$, the ratio of the feed flow to the organic phase reflux being 1:2 to 1:7 and 90 to 99% of the entire separated organic phase volume being refluxed. The acetic acid or the mixture of acetic acid and butanol fed into the system can contain also butylacetate and/or water. It is thus possible to feed e.g. a product of partial conversion of butanol-acetic acid mixture which contains at maximum the equilibrium concentration of butylacetate and water besides unreacted butanol and acetic acid.

The process according to this invention can be performed advantageously in an apparatus comprised of a column consisting of three zones, wherein the reaction zone placed in the middle part of the column contains a solid acidic catalyst immobilized in the reaction zone on distillation trays or by other systems known per se which ensure good contact between the liquid phase and the catalyst particles as well as between the liquid and the vapour phases in the countercurrent flow of these phases, e.g. the catalyst can be embedded in a structural packing with internal channel structure by fixing it between two layers of an inert porous material forming the structure of the packing; the lower and upper separation zones contain inert structural packings, common tower packings or distillation trays, the butanol feed pipe is connected through a closing valve to the acetic acid feed pipe, the joint feed is introduced into the reaction zone or above this zone, a second butanol feed pipe branch is connected to the reaction zone or below this zone being also equipped with a closing valve, a reboiler is connected to the column bottom, the butylacetate withdrawal line being conducted from the reboiler or the bottom, the column head which ends the upper part of the column is connected with the condenser by a vapour pipe, the condensate line leads from the condenser to the separator to the upper part of which a reflux pipe and a withdrawing pipe for the non-refluxed organic phase are connected while the water phase pipe is connected to the lower part of the separator.

In one possible arrangement, the butanol feed closing and control valve is closed, the pipe connection closing and control valve being open, in another arrangement, the butanol feed closing and control valve is open, the pipe connection closing and control valve being closed. Finally, both closing and control valves are open.

Besides feeding butanol and acetic acid independently into different points of the apparatus, the feed pipes configuration described above makes it possible to feed butanol or at least part of it in a mixture with acetic acid to one point in the reaction zone or in the upper separation zone, additional butanol being possibly fed by an independent feed line to the point in the reaction zone or in the lower separation zone placed below the butanol-acetic acid mixture feed point. The same effect can be achieved by preparing the butanol-acetic acid mixture separately, by means of some commonly known mixing device, feeding the mixture to the reaction zone or to the upper separation zone, additional butanol being fed into the reaction zone or into the lower separation zone without connecting both feed lines.

As can be seen from the description, the invention is based on discovery that butylacetate of sufficient quality can be prepared with advantage by the catalytic distillation method utilizing a distillation column consisting of a reaction zone which contains a solid acidic catalyst of common type, whilst there are inert separation zones placed both above and below the reaction zone. These separation zones contribute to establishing optimum concentration profiles of both starting compounds and products along the distillation column. As a result, maximum concentration of reacting compounds in the reaction zone is achieved and, consequently, high productivity of the equipment, optimum utilization of the catalyst as well as high product quality are achieved. Under the optimum conditions according to this invention, the purity of dry butylacetate, which is withdrawn from the reboiler, is above 99% mass.

Process for the Production of Isobutylacetate

Said drawbacks of the well known processes are overcome by the process for the production of isobutylacetate according to this invention, which consists in separately introducing acetic acid and isobutyl alcohol in a molar ratio of from 1:1 to 1:10 and in an amount, expressed as overall feed based on a volume unit of the catalyst, of 0.1 to 10 h$^{-1}$, in the presence of a solid acidic catalyst with simultaneous removing by distillation of the components, into a system where the reaction and the separation by distillation take place in three zones, wherein in the reaction zone the reaction runs simultaneously with the separation by distillation of the components with different boiling points and in the two separation zones only separation of the components by distillation takes place, water, formed as a by-product of the reaction, distilling out of the system in the form of a low-boiling azeotropic mixture, whereafter, the distillate being cooled down to 5 to 80° C., said water is separated from the organic portion of the distillate and withdrawn from the system, while the organic components of the distillate are refluxed back, the feeds of acetic acid and isobutyl alcohol being introduced into the system in such a manner that the acetic acid feed is introduced into inside the reaction zone or above this zone, namely into a point located higher than the isobutyl alcohol input, and the isobutyl alcohol feed is introduced into the reaction zone or below it, the ratio between the feed amount of the entering reactants and the refluxed organic phase being from 1:1 to 1:20 and the reflux representing from 50 to 100 per cent of the overall amount of the separated organic phase and isobutylacetate being separated as a higher-boiling bottoms product. Ion exchange resin, e.g. sulfonated styrene-divinylbenzene copolymer (1 to 25% of divinylbenzene) of acidity in the range from 1 to 10 meq H+/g, can be used as the catalyst. Different types of ion exchangers, zeolites or other commonly known acidic catalysts can be used as well.

In a preferred embodiment the process is performed at a molar ratio of acetic acid vs. isobutyl alcohol in the range of 1:1 to 1:1.5, the feed flow per the catalyst volume unit being 0.5 to 5 $h^{-1}$, the ratio of the feed flow to the organic phase refluxed being 1:2 to 1:7 and 80 to 99% of the entire separated organic phase volume being refluxed. A partially converted mixture of acetic acid and isobutylacohol can be fed instead of pure acetic so the acetic acid containing feed stream can contain also isobutylacetate and/or water and/or a certain part of unreacted isobutylacohol.

The process according to this invention is advantageously performed in an apparatus comprised of a column consisting of three zones, the reaction zone, placed in the middle part of the column, containing a solid acidic catalyst, in a preferred embodiment immobilized in well known types of structural packing with internal channel structure by fixing the catalyst between two layers of an inert porous material forming the structure of the packing; the lower and upper separation zones containing inert structural packings, common tower packings or distillation trays, the acetic acid feed pipe being introduced into the upper part of the reaction zone or above this zone while the isobutyl alcohol feed pipe is connected to the lower part of the reaction zone or below this zone, the column bottom being equipped with a reboiler, the isobutylacetate withdrawing line being conducted either from the reboiler or from the column bottom, the upper part of the column being furnished with a head equipped with a vapour pipe for introducing the distillate vapours into a condenser, from which a condensate line leads to the separator, to the lower part of which a water phase pipe is connected and to the upper part thereof a reflux line and a pipe for withdrawal of the non-refluxed organic portion of the distillate are connected.

It is apparent from the basic features of the invention described above, that it is possible to reach higher than equilibrium, practically up to 100%, conversion of starting compounds to isobutylacetate according to this invention. It is the main function of the separation zones to separate reaction products i.e. isobutylacetate and water from the starting components i.e. acetic acid and isobutyl alcohol and returning the starting components back to the reaction zone, while isobutylacetate is continually separated as a high boiling bottoms product and water is separated as distillate in the form of a volatile ternary heterogeneous azeotrope being withdrawn from the system after being separated from the organic phase of the distillate, which contains mainly isobutyl alcohol and isobutylacetate. The organic phase is entirely or partly refluxed. The amount ratio of starting components fed to the organic phase reflux is 1:1 to 1:20, the reflux representing 50 to 100% of the whole amount of separated organic phase.

Starting components i.e. acetic acid and isobutyl alcohol can be fed either in equimolar ratio, or some excess of isobutyl alcohol can be applied to convert all acetic acid. If the process according to this invention is run under atmospheric pressure, the following temperature profile is established: 110 to 120° C. in the reboiler and 87 to 104° C. in the head of the column. The process according to the invention can also be performed under reduced pressure. Isobutyl alcohol is introduced below the acetic acid input. Most commonly, isobutyl alcohol is introduced below the reaction zone or into its lower part, while acetic acid is introduced above said zone or into its upper part.

The vapours carried out of the column head condense yielding a mixture which is separated into water and organic phases after being cooled at 80 to 5° C. Whole amount, or the major part of the organic phase is refluxed to the column head. The water phase containing dissolved isobutyl alcohol and isobutylacetate is taken off. The alcohol and ester dissolved can be stripped from the water phase and returned to the process. The desired reaction product—dry isobutylacetate is withdrawn from the reboiler at the temperature of 110 to 120° C. The product purity depends both on the molar ratio and the amount of starting components introduced to the system and on the catalyst to starting components amount ratio as well as on the catalyst activity. The product obtained is of commercial quality or it is easy to improve its quality to that level by non demanding consequent distillation.

Figure 1:
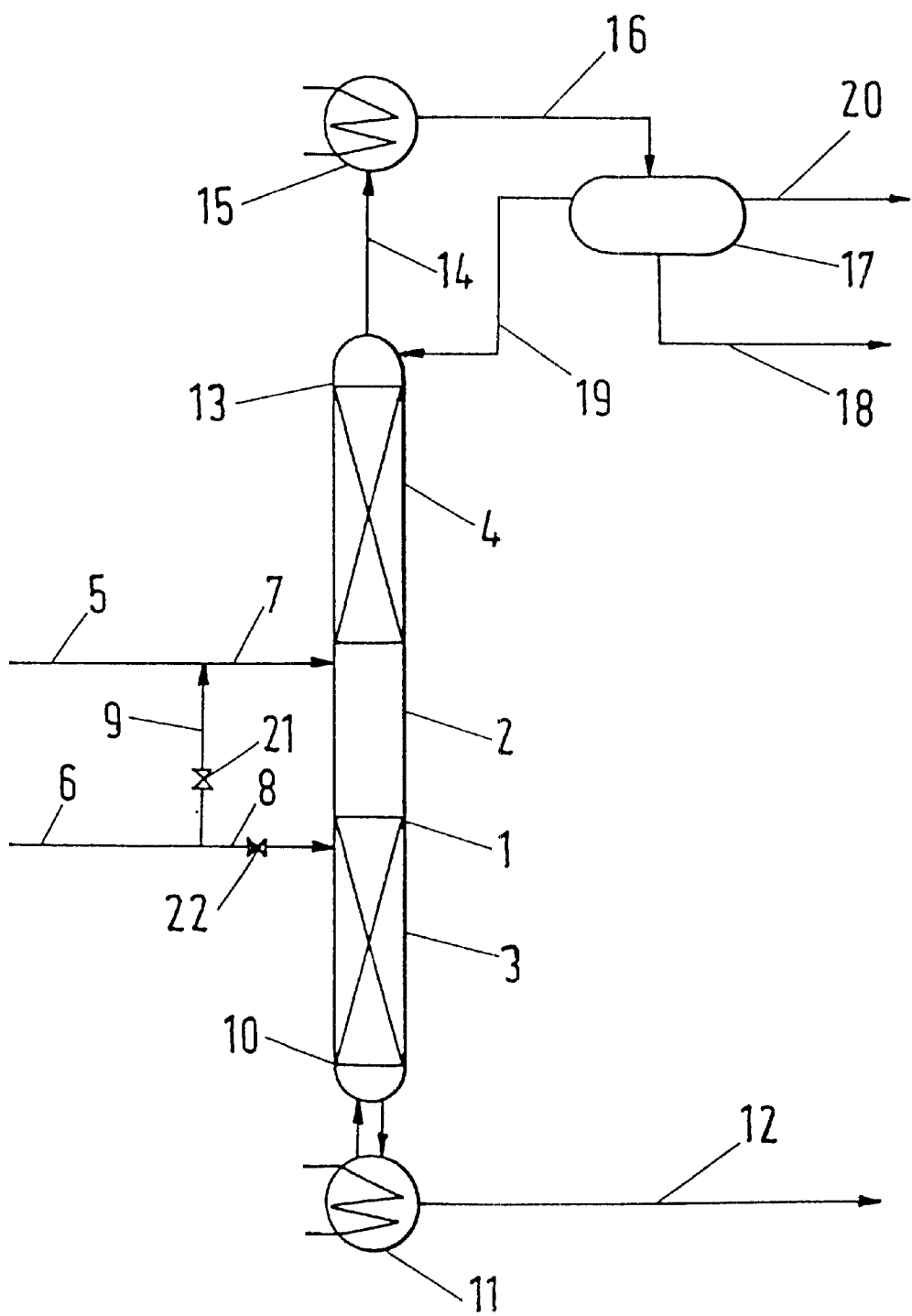
FIG. 1 represents an apparatus for performing the process for the production of butylacetate according to the invention. The apparatus consists of a column 1 containing three zones, the reaction zone 2 containing a solid catalyst is placed in the middle part of the column 1 while the lower separation zone 3 as well as the upper separation zone 4 are packed with structural packings, common tower packings or distillation trays, acetic acid feed pipe 5 is connected with butanol feed pipe 6 by a line 9 which is furnished with a closing and control valve 21, a feed line 7 is introduced into the reaction zone 2 or above the top of this zone while the butanol feed line 6 is connected to a separate butanol input 8, which is also furnished with a closing and control valve 22, being introduced into the reaction zone 2 or below this zone. Reboiler 11 is linked to the bottom 10 of the column 1, butylacetate withdrawal line 12 is conducted from reboiler 11 or bottom 10, the column head 13 is connected with condenser 15 by vapour flow line 14, the condenser 15 being connected with phase separator 17 by the condensate flow line 16, water phase flow line 18 is connected to the lower part, while reflux flow pipe 19 and organic phase flow line 20 are attached to the upper part of the separator 17.

The process according to this invention is performed by means of the above described apparatus as follows: acetic acid feed 5 and butanol feed 6 are either mixed together to be introduced into the reaction zone 2 by joint feed line 7 or they can be introduced into the column 1 individually. Therefore, butanol input line 6 is either introduced into acetic acid feed pipe 5 or it is directly introduced through feed point 8 into the reaction zone 2, or, possibly, below this zone both routes being in this case separated by valve 21. Butylacetate is withdrawn via line 12 from reboiler 11, alternatively from column bottom 10. Distilling vapours, containing water, part of butylacetate and unreacted butanol are passed from column head 13 to condenser 15 and, finally, to separator 17. The water phase is taken off by line 18, the organic phase is completely or partially refluxed to column 1 above the upper separation zone 4 by line 19. A portion of the organic components can be withdrawn.

Figure 2:
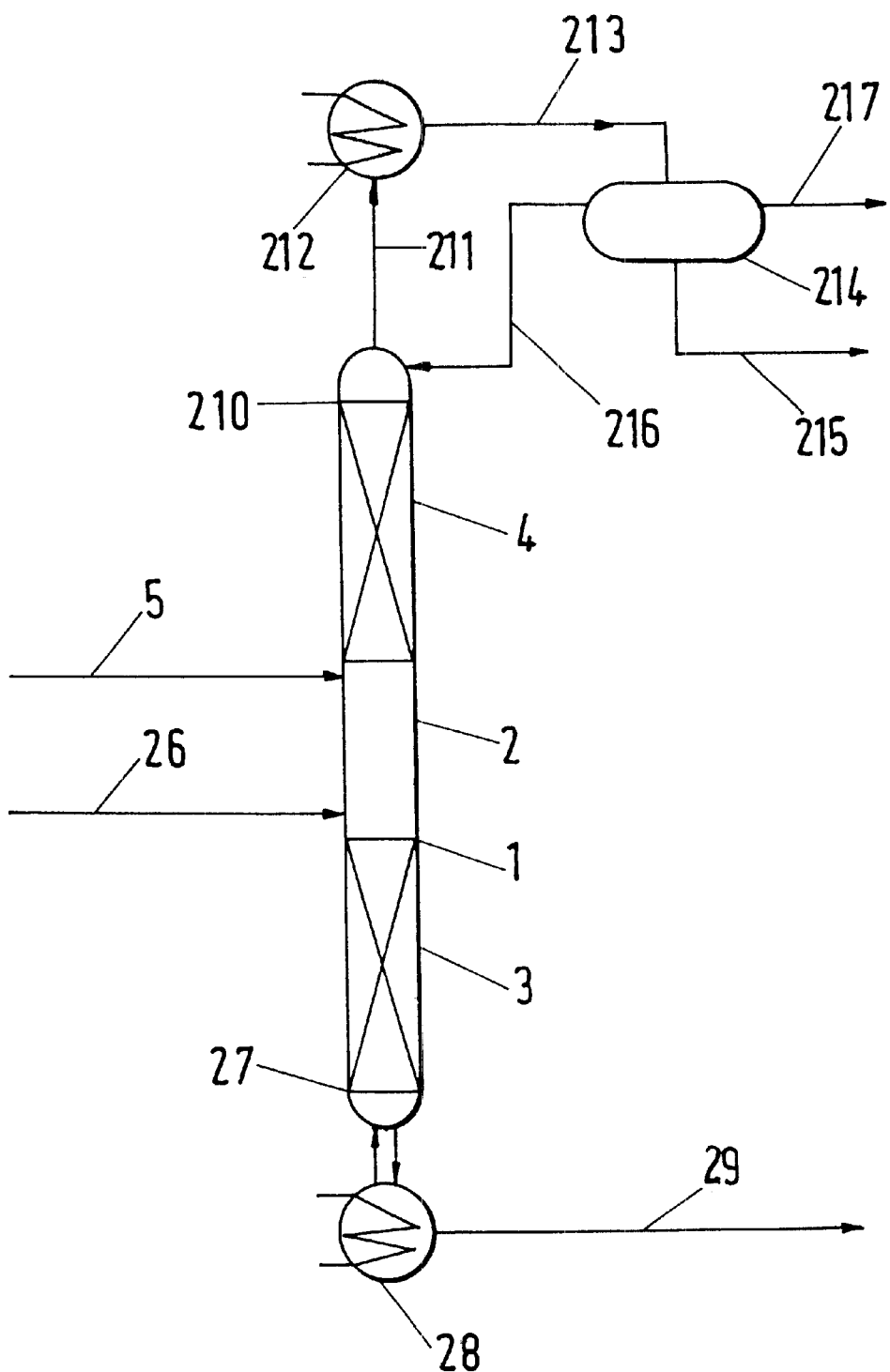

FIG. 2 presents an apparatus for performing the process for the production of isobutylacetate according to the invention. The apparatus consists of a column 1 containing three zones, the reaction zone 2 containing a solid catalyst is placed in the middle part of the column 1 while the lower separation zone 3 as well as the upper separation zone 4 are packed with structural packings, common tower packings or distillation trays, acetic acid feed pipe 5 is connected to the upper part of the reaction zone 2, isobutyl alcohol feed pipe 26 is linked to the lower part of the reaction zone 2, column bottom 27 ends up the lower part of column 1, the bottom 27 being linked to reboiler 28, to which isobutylacetate withdrawing line 29 is connected, column head 210 ends up the upper part of the column, vapour flow line 211 is connected to column head 210 and to condenser 212 which is connected with separator 214 by condensate flow line 213, water phase flow line 215 is connected to the lower part while reflux flow line 216 and the unrefluxed organic phase withdrawing flow line 217 are connected to the upper part of separator 214.

The process according to this invention is performed by means of the above described apparatus as follows: acetic acid feed 5 is introduced into the lower part of the upper separation zone 4 or into the upper part of the reaction zone 2, while isobutyl alcohol feed 26 is introduced into the upper part of the lower separation zone 3 or into the lower part of the reaction zone 2, isobutylacetate formed by the reaction is withdrawn by line 29 from reboiler 28 or, alternatively, from column bottom 27, distilling vapours, containing water, part of isobutylacetate and unreacted isobutyl alcohol are passed from column head 210 to condenser 212 and, finally, to separator 214 where water is separated from organic compounds, the organic phase being completely or partly refluxed to column 1. Certain portion of the organic phase can be taken off.

Modes for Carrying Out the Invention

EXAMPLE 1

The apparatus utilized for performing the process according to the invention is schematically presented in FIG. 1. A distillation column 1 operating under atmospheric pressure consisted of three zones. There was the reaction zone 2 in the middle part of the column 1, the lower separation zone 3 was placed below, while the upper separation zone 4 above the reaction zone 2. Reboiler 11 was connected to bottom 10, condenser 15 was connected to column head 13 and to separator 17.

The reaction zone 2 was packed with an active packing containing 33 g of acidic ion exchange resin. Both the lower separating zone 3 and the upper separating zone 4 were packed with common tower packing—Berl saddles of characteristic dimension 4 mm. The lengths of the separation zones 3 and 4 was 0.5 m.

The Process Was Performed as Follows

Acetic acid feed 7 was introduced above while butanol feed 8 was introduced below reaction zone 2. Both these starting components were fed at a rate of 0.3 mole per hour. Vapours 14 passed from column head 13 to condenser 15. Condensed liquid was carried via 16 from condenser 15 to phase separator 17. Reaction water was withdrawn in the amount of 5 g/h from phase separator 17 as the water phase 18, while the organic phase of the distilled azeotrope was refluxed via 19 to column 1. Crude butylacetate was taken off via 12 from reboiler 11 at a velocity ensuring constant holdup in reboiler 11. Conversion was 92%, the product taken off via line 12 contained 90.9% mass. of butylacetate in this regime.

EXAMPLE 2

An equimolar mixture of acetic acid and butanol was injected at the rate of 40.3 g/h into the apparatus described in example 1. 2.2 g/h of butanol were injected by line 8 below the reaction zone 2. 5.5 g/h of organic distillate were withdrawn by line 20. 32 g/h of the product containing 94.5% mass of butylacetate were withdrawn from reboiler 11.

EXAMPLE 3

Esterification of butanol with acetic acid was performed by means of an apparatus consisted of reboiler 11 the volume of which was 50 dm$^3$ and distillation column 1 equipped with condenser 15 and phase separator 17. The reaction distillation column 1 consisted of the reaction zone 2 packed with KATAPAK® S structural packing containing 710 g of an acidic ion exchange resin in H$^+$ form, both the lower 3 and upper 4 separation zones were packed with CY® structural packing, the each zone efficiency equivalent to 20 theoretical stages. 1.21 kg per hour of a mixture containing 43.3% mass. of acetic acid and 56.6% mass. of butanol was injected at the boundary between the reaction zone 2 and the upper separation zone 4 through feed line 7. Vapours 14 condensed in condenser 15, the condensate 16, the temperature of which was 35° C., was divided into water and organic phases in separator 17. The water phase was taken off via 18, whole volume of the organic phase was refluxed to the head of the column 13 via 14. Butylacetate of 96.01 mass. % purity was withdrawn via 12 from reboiler 11 at the rate of 1.05 kg per hour.

EXAMPLE 4

Both the apparatus and the process were the same as described in example 3. The feed stream 7 contained 14.16 mass. % of acetic acid, 20.74 mass. % of butanol, 57.32 mass. % of butylacetate and 7.8 mass. % of water. The feed rate was 2.20 kg per hour. The mixture of this composition had been obtained by preliminary partial conversion of an acetic acid-butanol mixture in a reactor of common type packed with an acidic ion exchange resin. Butylacetate of 99.4 mass. % purity, containing 0.06 mass. % of acetic acid and 0.25 mass. % of butanol was withdrawn via 12 from reboiler 11 at a rate of 1.91 kg per hour.

EXAMPLE 5

1.92 kg per hour of a mixture containing 15.1 mass. % of acetic acid, 19.2 mass. % of butanol, 55.84 mass. % of butylacetate and 9.9 mass. % of water was injected by feed line 7 into the column described in example 3. 0.0418 kg/h of organic phase from the distillate were taken off by line 20. 1.62 kg per hour of butylacetate of 99.5 mass. % purity were withdrawn from reboiler 11. No acetic acid was detected by the gas chromatography method in this product.

EXAMPLE 6

The apparatus was identical as in examples 3–5. 2.80 kg/h of a mixture containing 13.16 mass. % of acetic acid, 21.58 mass. % of butanol, 56.52 mass. % of butylacetate and 8.72 mass. % of water was injected by feed line 7. 0.0642 kg/h of organic phase from the distillate were taken off by line 20. 2.39 kg per hour of butylacetate of 99.2 mass. % purity were withdrawn from reboiler 11. No acetic acid was detected by the gas chromatography method in this product.

EXAMPLE 7

A mixture containing 17.9% mass of butanol, 14.5% mass of acetic acid, 58.4% mass of butylacetate and 9.4% mass of water was injected by feed line 7 into the apparatus of the same construction as described in examples 3–6, the feed rate being 1.85 kg/h. At the same time 29.6 g/h of butanol were injected by line 8 between the reaction zone 2 and the lower separation zone 3. The column head pressure was 600 mbar. The organic phase of the distillate was withdrawn at the rate of 0.02 kg/h by line 20. 1.56 kg/h of the product containing 99.3% mass of butylacetate, 0.5% mass of acetic acid and 0.2% mass of butylacetate were withdrawn from reboiler 11.

EXAMPLE 8

The apparatus utilized for performing the process of the production of isobutylacetate according to the invention is schematically presented in FIG. 2. A catalytic distillation column 1, operating continually under atmospheric pressure, was divided into three zones. There was the reaction zone 2 in the middle part of the column 1, the lower separation zone 3 was placed below, while the upper separation zone 4 above the reaction zone 2. Reboiler 28 was connected to bottom 27, condenser 212 was connected to column head 210 and to separator 214.

The reaction zone 2 was packed with an active packing containing 33 g of an acidic ion exchange resin. Both the lower separating zone 3 and the upper separating zone 4 were packed with common tower packing. Berl saddles of characteristic dimension 4 mm. The lengths of the separation zones 3 and 4 were 0.5 mm.

The Process Was Performed as Follows

Isobutyl alcohol was fed via 26 to the lower separation zone 3, while acetic acid was introduced into the upper separation zone 4 via 5. Both said starting components were introduced at a rate 0.3 moles per hour. The vapours were passed from column head 210 to condenser 212 via 211. The condensate was carried from condenser 212 to separator 214 via 213. The water formed by the reaction was taken off at a rate of 4.9 g/h from separator 214 as the water phase 215, while the whole amount of organic phase separated from the azeotrope was refluxed via 216 into the column. 33 g per hour of crude isobutylacetate were withdrawn from reboiler 28 through isobutylacetate line 29. Conversion was 92% in this embodiment.

EXAMPLE 9

The esterification of isobutyl alcohol with acetic acid was performed by means of an apparatus consisting out of a reboiler 28 the volume of which was 50 dm$^3$ and a catalytic distillation column 1 equipped with a condenser 212 and a phase separator 214. The reaction distillation column 1 consisted of the reaction zone 2 packed with KATAPAK® S structural packing containing 710 g of an acidic ion exchange resin in H$^+$ form, both the lower 3 and upper 4 separation zones were packed with structural packing, the efficiency of each zone responding to 10 theoretical stages. Acetic acid was fed via 5 in the amount of 0.55 kg/h into the reaction zone 2 while 0.75 kg/h of isobutyl alcohol was injected via 26 to the top edge of the lower separation zone 3. The water formed by the reaction was taken off via 215 from separator 214, the organic phase was refluxed via 216 to column 1, a part of the organic phase (37 g/h) was withdrawn as distillate 217. A constant holdup was maintained in reboiler 28 by taking off the crude isobutylacetate via 29. This product contained 0.1 mass % of acetic acid and 4.8 mass % of isobutyl alcohol.

EXAMPLE 10

Both the apparatus and the process were the same as described in example 2. Both the lower separation zone 3 and the upper separation zone 4 were packed with structural packing of the efficiency equal to 20 theoretical stages. Acetic acid was injected into the system in the amount of 0.65 kg/h, the isobutyl alcohol feed amount being 1.02 kg/h. The amount of water phase withdrawn from separator 214 was 0.172 kg/h, the organic phase separated in separator 214 was refluxed into column head 210 at a rate 9.0 kg/h, while 0.43 kg/h of this phase were withdrawn via 217. Isobutylacetate of 99 mass % purity was withdrawn from reboiler 28 in the amount of 1.07 kg/h.

EXAMPLE 11

The column setup was the same as described in examples 9 and 10. The difference was that the efficiency of lower separation zone was equal to 15 theoretical stages while that of upper separation zone 4 was 25 theoretical stages. Both starting components were fed into the system at the same velocity like in example 10. Isobutylacetate of 98.9 mass % purity was withdrawn from reboiler 28 in the amount of 1.072 kg/h.

INDUSTRIAL APPLICABILITY

The invention can be utilized in chemical industry. The product is utilizable as a solvent mainly in paints and coatings manufacture as well as an extraction solvent in pharmaceutical industry, biotechnology and other branches of industry.

What is claimed is:

1. Process for the production of butylacetate by esterification of acetic acid with butanol in the presence of a solid acidic catalyst, accompanied by the distillation separation of the components involved, characterized by introducing acetic acid and butanol in the molar ratio of 1:1 to 1:10, the entire amount of the feed per volume unit of the catalyst being 0.1 to 10 h$^-$, into a system in which a reaction and separation by distillation take place in first, second and third zones, the reaction running simultaneously with separation by distillation of the compounds of different boiling points in the reaction zone, while the separation of components by distillation takes place in upper and lower separation zones, namely a volatile fraction is separated in the upper separation zone, which, after being cooled to 5 to 80° C., is split into water and organic phases, the organic phase being refluxed to the reaction, the ratio of the feed to the refluxed organic phase being 1:1 to 1:20, the reflux representing 60 to 100% of the separated organic phase and butylacetate being withdrawn as a high boiling bottoms product.

2. The process according to claim 1 characterized by introducing acetic acid and butanol into the system as a mixture.

3. The process according to claim 1 characterized by introducing acetic acid and butanol into the system separately, acetic acid being introduced into the reaction zone or into an upper separation zone, and the butanol being introduced into the reaction zone or into a lower separation zone of the system.

4. The process according to claim 1 characterized by introducing 1 to 99% of butanol into the reaction zone or into the upper separation zone as a mixture with acetic acid, and introducing 99 to 1% of starting butanol separately into the reaction zone or into the lower separation zone at the same time.

5. The process according to claim 1 characterized by introducing acetic acid and butanol into the system in a molar ratio of 1:1 to 1:1.3.

6. The process according to claim 1 and maintaining the entire feed rate of starting compounds per a volume unit of catalyst in the range of 0.5 to 5 h$^{-1}$.

7. The process according to claim 1 characterized in that the ratio of feed amount to the organic phase reflux amount is in the range 1:2 to 1:7.

8. The process according to claim 1 wherein the reflux amount represents 90 to 99% of the entire amount of the organic phase separated from the distillate.

9. The process according to claim 1 characterized that acetic acid or the mixture of acetic acid with butanol introduced into the system contains also butylacetate and/or water.

10. A process for producing isobutylacetate by esterification of acetic acid and isobutyl alcohol in the presence of a solid acetic catalyst and simultaneous separation of components by distillation comprising individually introducing acetic acid and isobutyl alcohol in a molar ratio of from 1:1 to 1:10 and in an amount, expressed as overall feed based on a volume unit of the catalyst, of 0.1 to 10 $h^{-1}$, into a system in which the reaction and the separation by distillation take place in zones, the reaction running simultaneously with the separation by distillation of components with differing boiling points in a reaction zone and separation of the components by distillation takes place in first and second separation zones, water, formed as a side product of the reaction and forming a low-boiling azeotropic mixture with isobutyl alcohol and isobutylacetate, distilling out of the system, thereafter cooling the distillate to 5 to 80° C., separating the water from an organic portion of the distillate and withdrawing it from the system while the organic components of the distillate are refluxed back, introducing feeds of acetic acid and isobutyl alcohol into the system in such a manner that the acetic acid feed is introduced into the reaction zone or above the reaction zone at a point located higher than an isobutyl alcohol input, and introducing the isobutyl alcohol feed into the reaction zone or below the reaction zone, a ratio between the feed of the entering reactants and the refluxed organic phase being from 1:1 to 1:20 and the reflux representing from 50 to 100% of the separated organic phase and isobutylacetate being separated as a higher boiling bottoms product.

11. A process according to claim 10 characterized by introducing acetic acid and isobutyl alcohol in a molar ratio of 1:1 to 1:1.5.

12. A process according to claim 10 wherein the entire feed rate of starting compounds per volume unit of catalyst is in the range of 0.5 to 5 $h^{-1}$.

13. A process according to claim 10 wherein the ratio of feed amount to the organic phase reflux amount is in the range of 1:2 to 1:7.

14. A process according to claim 10 wherein the reflux amount represents 80 to 99% of the entire organic phase separated from the distillate.

15. A process according to claim 10 wherein the acetic acid introduced into the system contains at least one of isobutylacetate, water and isobutylalcohol.

* * * * *